US00PP08290P

United States Patent [19]

Carmel

[11] Patent Number: Plant 8,290

[45] Date of Patent: Jul. 6, 1993

[54] ROSE PLANT—CAROLA

[75] Inventor: Carmi Carmel, Moshav Hayogev, Israel

[73] Assignee: Yuval Agricultural Products Ltd., Israel

[21] Appl. No.: 767,546

[22] Filed: Sep. 27, 1991

Related U.S. Application Data

[63] Continuation of Ser. No. 387,837, Aug. 1, 1989, abandoned.

[30] Foreign Application Priority Data

Jan. 12, 1989 [IL] Israel ..... 1392/89

[51] Int. Cl.[5] ..... A01H 5/00

[52] U.S. Cl. ..... Plt./20

[58] Field of Search ..... Plt./20, 19, 21

[56] References Cited

U.S. PATENT DOCUMENTS

P.P. 4,391 3/1979 Delbard ..... Plt. 20

4,724,276 2/1988 Ecke, Jr. ..... 47 58

FOREIGN PATENT DOCUMENTS 855 6/1978 France .

OTHER PUBLICATIONS

Haring P. A. (Ed.) *Modern Roses 9,* Amer. Rose Society, 1986, p. 181.

*Primary Examiner*—James R. Feyrer

*Attorney, Agent, or Firm*—Pollock, Vande Sande & Priddy

[57] ABSTRACT

A rose plant exhibiting good resistance to powdery mildew, and being characterized by nonfragrant flowers, very high crop, good self-rooting and high stem break forth.

2 Drawing Sheets

This application is a continuation application of application Ser. No. 07/387,837, filed Aug. 1, 1989, now abandoned.

FIELD OF THE INVENTION

The present invention is concerned with a new variety of hybrid tea rose discovered by me and being a mutation of Deladel (U.S. Plant. Pat. No. 4,391, dated Mar. 6, 1979), Madame G. Delbard variety.

SUMMARY OF THE INVENTION

The mutation was first discovered on a cultivated area, in a farm located in South America, at an altitude of about 2,400–2,500 meters above sea level, with average night temperature of 5–8 degrees centigrade, and day temperature of 5–18 degrees centigrade.

Plants were grown in a green-house, and then brought to Israel, where they were vegetatively propagated by selfrooting of cuttings.

Asexual reproduction of this new cultivar as performed at Yuval Agriculture Products at Moshav Ha'Yogev shows that the foregoing characteristics and distinctions came true to form and are established and transmitted through succeeding propagations.

The resulting plants were found to be stable in their botanical characteristics, as are described below and in the attached drawing.

The following is a description of the characteristics of my new rose cultivar which distinguish it from cultivars of which I am aware and especially from Madame G. Delbard (Deladel):

1. Better branching.
2. Larger flower bud.
3. Distinct larger number of petals.
4. Larger sepals with larger extensions.
5. More water shoots, than the original plant.
6. Good grafting compatibility on *Rosa indica* L.

BRIEF DESCRIPTION OF THE DRAWING

The first sheet of the drawing depicts buds of the claimed plant in various stages of opening; the characteristic shape and foliaceous appendages of the sepals are shown along with the high-centered character of the buds themselves. The coloration of the other surfaces of the petals at this stage of opening is also depicted.

The second sheet of drawing shows, in comparison, two petals of Carola, designated as A at the top of the drawing, and petals of comparable stage of maturity as taken from the parent variety "Deladel", labelled B, at the bottom of the drawing. This sheet of drawing also depicts the typical difference in size of the petals taken from the mutation as compared to the parent variety; and, also shows the difference in the size of the spot at the point of petal attachment; that of the parent "Deladel" being much smaller in the comparison; and the difference in coloration; that of the sport being clear white while that of the parent being light yellow in color.

DETAILED DESCRIPTION OF THE INVENTION

The following is a detailed description of my new rose cultivar with color in terminology in accordance with Royal Horticultural Society of London, England (R.H.S.) Colour Chart except where ordinary dictionary significance of color is indicated.

The plant originated from a mutation of Madame G. Delbard.

The following description is based on observations made in Moshav Ha'Yogev, Israel, in a greenhouse:

| Plant | growth habit | upright |
|---|---|---|
| Older stem | | corky[1] |

-continued

| Plant | growth habit | upright |
|---|---|---|
| Young shoot | anthocyanin coloration | strong |
| | hue of anthocyanin coloration | purple |
| Prickles | | present |
| Prickle | shape of upper sides | straight |
| | shape of lower side | concave |
| Short prickles | number | few |
| Long prickles | number | few |
| Leaf | size | length 140–170 mm<br>width 110–150 mm |
| | green color | medium to dark |
| | glosssiness of upper side | absent or very weak |
| Leaflet | cross section | slightly convex |
| | undulation of margin | absent or very weak |
| Terminal leaflet | length of blade | ca. 60 mm |
| | maximum width | ca. 35 mm |
| | length of petiole | ca. 20 mm |
| | shape of base | rounded |
| Flowering shoot | number of flowers | few |
| Flowering habit | | continuous |
| Flower pedicel | number of hairs or prickles | few |
| Flower bud | longitudinal section | circular to ovoid |
| Flower | type | double |
| | number of petals | 33–40 |
| | diameter | ca. 110 mm |
| | view from above | rounded to star-shaped |
| | side view of upper part | flattened-convex |
| | side view of lower part | flat |
| | fragrance | none |
| Sepal | length | 40–55 mm |
| | extensions | strong |
| Petal | size | length 50–60 mm<br>width 55–65 mm |
| | shape | rounded |
| | color of middle zone of inner side (according to the Royal Horticultural Society Color Chart) | RHS 53-A dark red |
| | color of marginal zone of inner side | RHS 53-A dark red |
| | spot at base of inner side | present |
| | size of spot at base of inner side | medium (length of spot on the upper side of the petal was 8–10 mm) |
| | color of spot at base of inner side | white (RHS 155-D) |
| | color of middle zone of outer side | RHS 53-C dark red |
| | color of marginal zone of outer side | RHS 53-C dark red |
| | spot of base of outer side | present |
| | size of spot at base of outer side | very small to small |
| | color os spot at base of outer side | white |
| | reflexing of margin | strong |
| | undulation of margin | weak |
| Stamen | predominant color of filament | purple |
| | length | long |
| | predominant color | purple |
| | hairiness of upper half | medium |
| | position as compared with anthers | above |

-continued

| Plant | growth habit | upright |
|---|---|---|
| | size | medium |
| | shape of longitudinal section | pitcher shaped |

[1]Typical for hybrid tea roses.

The time of beginning of flowering is early.

The average number of petals per flower: 33–38.

The bud size at time of picking is 5–6 cm long, and 3 cm in diameter.

The number of side shoots per flowering branch is 5–6.

The annual produce is 150–160 flowers per square meter.

Flowering stem medium green, 70–80 cm long with an average of 13 leaves.

The vase life is up to 15 days, under condition of room temperature.

Average number of water shoots, in 1st year after planting 4–6.

Prickles, per internode — 2–3.

Prickles up to 3rd leaf — 1.

Number of leaflets per leaf — 5–7.

Budding sprout — 8–9.

Fragrance — none.

Plant's height in 8 months after planting 170–180 cm.

Time from planting to commercial flower production 6–8 months.

Good resistance to Rose Powdery Mildew.

Exhibits high stem break forth, very high crop and good self-rooting.

Under condition of room temperature flower opening proceeds

Under condition of room temperature flower opening proceeds slowly.

The variety should be grown under glass.

Comparison Of Production Characteristics Between The New Variety "Carola" and Variety "Deladel"

Observations made in Ecuador from commercial plantings during 1988–1990, where the two varieties were grown side by side, under the same conditions and same age, were both self-rooted and with the same planting time. Each one 10,000 square meters of plants.

| | Carola | Deladel |
|---|---|---|
| Average number of petals | 33–38 | 18–25 |
| Average number of cut flowers per plant per month (year round production) | 1.85–2.00 | 0.90–1.25 |
| Average number of water-shoots in first year after planting | 4–6 | 2–3 |
| Plant height in 8 months after planting | 170–180 cm | 80–90 cm |
| Size of spot at base of inner side | medium | very small |
| Color of spot at base of inner side of petal | white (RHS 155-D) | yellow |
| Fragrance of flower | none | slight, not sweet of spicy |
| Time from planting to commercial flower production | 6–8 months | 10–12 months |
| Grafting compatibility on Rosa indicia L. | very good (about 65% success) | very poor |

The size of the spot was, for the variety 'Carola' defined as: size of spot at base of inner side of petal-medium, and size of spot at base of outer side of petal-very small to small, using the sketch of the Test Guidelines for Rose of the Union for Protection of New Plant Varieties (document TG/11/4)-applying the following calculation:

$$[1+\{(\text{average length of spot/average length of petal})-1\}]/(35-1)*8$$

With lower value of length of spot 1 mm, and higher value of length of spot 35 mm.

Statistical Analysis For Additional Observations Made In Ecuador In Order To Compare Carola With Deladel

| | Carola | Deladel |
|---|---|---|
| Number of petals: | | |
| standard deviation | 7.77 | 3.92 |
| mean | 32.05 | 22.35 |
| Plant height in 8 months: | | |
| standard deviation | 0.13 | 0.10 |
| mean | 1.97 | 1.50 |
| Basal shoots: | | |
| standard deviation | 1.48 | 0.67 |
| mean | 3.00 | 1.32 |
| Flowers per plant: | | |
| standard deviation | 0.53 | 0.48 |
| mean | 1.76 | 1.17 |

In all tests of the examined characteristics, the conclusion was that the population differ with a high level of significance.

Comparison Of Production Characteristics Between The New Variety Odem And Variety Carola The new variety Odem is a variety that was subsequently discovered and is a spot of Carola. They differ as described below:

| | Odem | Carola |
|---|---|---|
| Average number of petals | 39–48 | 33–38 |
| Size of petal | | |
| length | 37–45 mm | 50–60 mm |
| width | 39–49 mm | 55–60 mm |
| Flower | | |
| diameter | ca. 80 mm | ca. 100 mm |
| color of upper side | RHS 46-AB | RHS 53-A |
| Petal's reflexing | medium | strong |
| Size of spot at base of inner side of petal | small | medium |
| Color of spot at base of inner side | yellow | white |
| Length of flowering stem | 50–70 cm | 70–90 cm |
| Thickness of flowering stem | medium | thick |
| Number of flowering stems per plant per year | about double as for Carola | |

I claim:

1. A new and distinct variety of rose plant of a hybrid tea rose, variety, named Carola, as shown and described, and consisting mainly of plants being vigorous growing, showing a large flower bud, containing a large number of petals, having nonfragrant with petals with a medium-sized white spot at their base, with early and prolific flower production, and having fast and good propagating features.

* * * * *

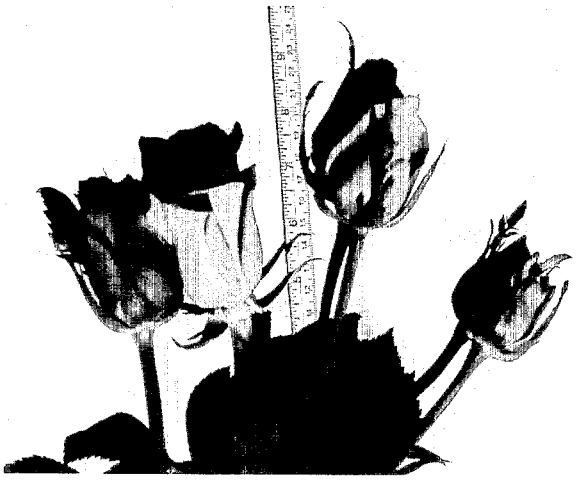

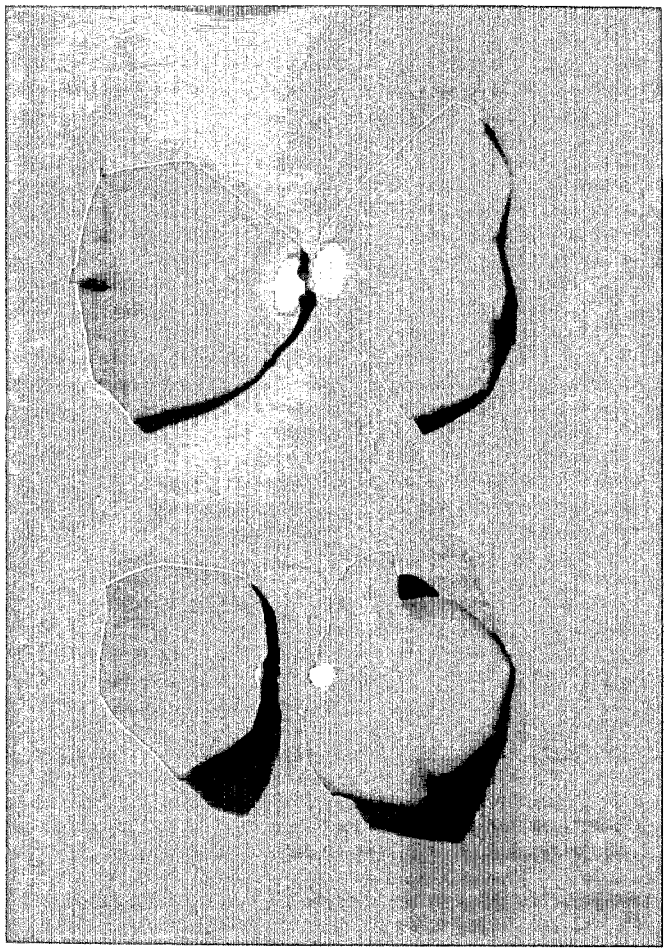
A
B